Figure 1:
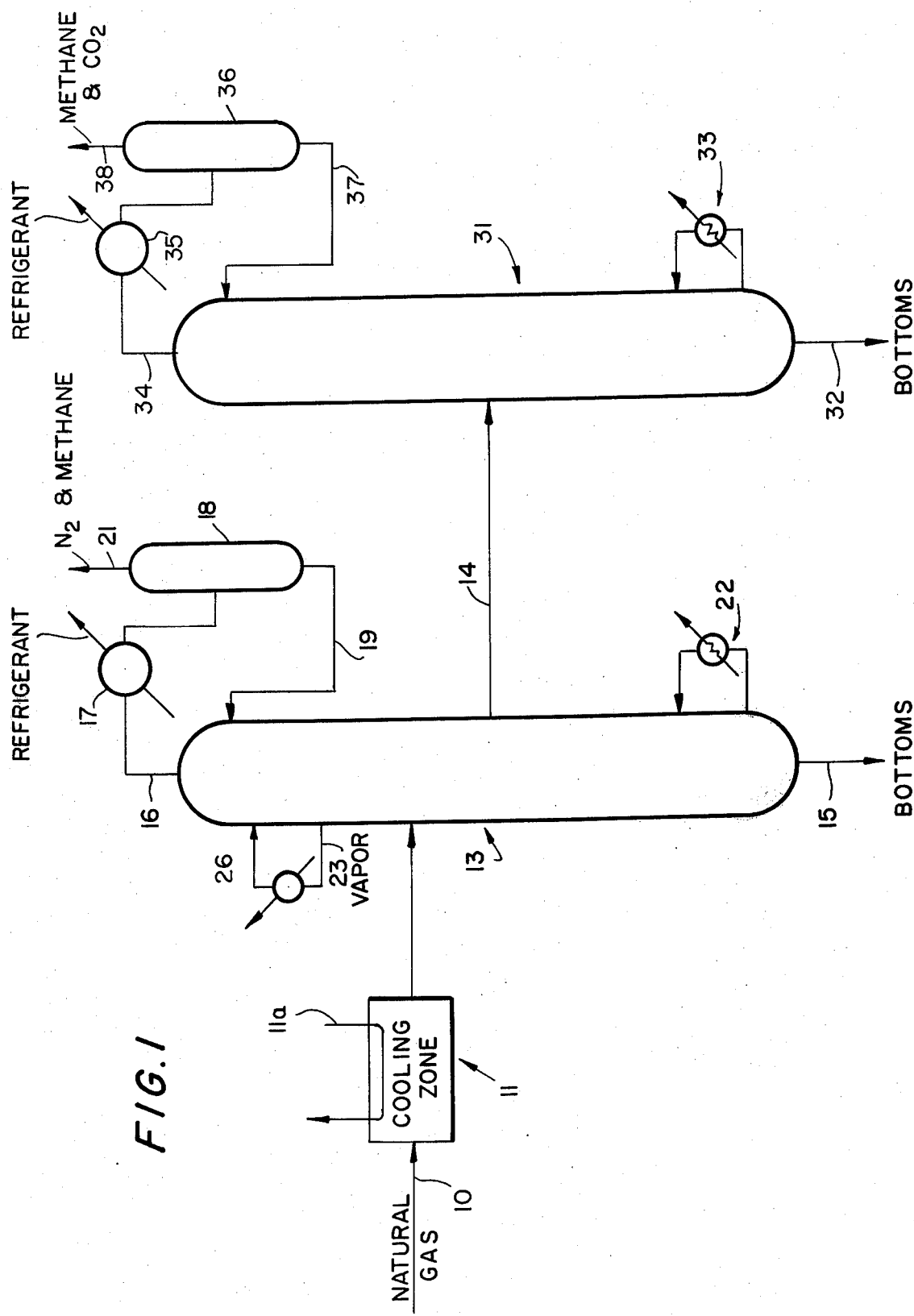

United States Patent [19]
Solomon

[11] 3,983,711
[45] Oct. 5, 1976

[54] PLURAL STAGE DISTILLATION OF A NATURAL GAS STREAM

[75] Inventor: Stephen M. Solomon, New York, N.Y.

[73] Assignee: The Lummus Company, Bloomfield, N.J.

[22] Filed: Jan. 2, 1975

[21] Appl. No.: 538,191

[52] U.S. Cl. .................... 62/28; 62/30; 62/31; 62/39
[51] Int. Cl.² .......................... F25J 3/02
[58] Field of Search .................. 62/23–29, 62/9, 11, 36, 38, 39, 42, 31–34

[56] References Cited
UNITED STATES PATENTS
2,826,266  3/1958  Hachmuth et al. .......... 62/23
3,130,026  4/1964  Becker .................... 62/24

Primary Examiner—Frank W. Lutter
Assistant Examiner—Frank Sever
Attorney, Agent, or Firm—Marn & Jangarathis

[57] ABSTRACT

Natural gas, containing carbon dioxide and nitrogen, is demethanized in a first fractional distillation tower to provide an overhead of nitrogen and methane free of carbon dioxide and components heavier than methane. A sidestream is withdrawn from the first tower at a point therein where carbon dioxide concentration is maximized and the sidestream is fractionated in a second tower to recover methane and carbon dioxide as overhead. Nitrogen is rejected from the carbon dioxide free overhead from the first tower by liquefaction of methane to provide a send-out gas free of nitrogen. The cold potential of various streams is used to provide cooling requirements for the process.

14 Claims, 2 Drawing Figures

PLURAL STAGE DISTILLATION OF A NATURAL GAS STREAM

This invention relates to the treatment of natural gas. More particularly, this invention relates to the recovery of a stream comprised of nitrogen and methane, essentially free of carbon dioxide and components heavier than methane, from a natural gas stream containing methane, nitrogen and carbon dioxide. Still more particularly, this invention relates to a new and improved process for providing, from natural gas, rich in nitrogen and carbon dioxide, a stream of methane, essentially free of nitrogen, carbon dioxide and components heavier than methane.

Many natural gas sources contain appreciable quantities of nitrogen, carbon dioxide, and ethane plus heavier hydrocarbons. In many cases, it is desirable to treat the natural gas to recover ethane and heavier components thereof. The recovery of ethane and heavier components reduces the heating value of the remaining gas and, consequently, the necessity often arises to reject nitrogen from the gas in order to increase the sales gas heating value. In separating the nitrogen from methane, by low temperature flash or rectification steps, the presence of small quantities of carbon dioxide can cause solidification of the carbon dioxide. In order to prevent such freezing, the carbon dioxide is generally separated from the natural gas before entering the cold separation section of the process. In general, the carbon dioxide is removed from the natural gas by the use of a suitable acid gas absorption solvent, such as, one of the monoethanol amines. The natural gas is contacted by the acid gas absorption solution, and the carbon dioxide is then chemically absorbed in the solution. This system requires the installation of an absorber and a solvent regenerator in order to both absorb the carbon dioxide and regenerate the acid gas absorption solution. The installation of such equipment increases the capital cost of the plant. In addition, the utilities requirements of the plant are increased by the necessity of employing heat for the regenerator reboiler. Furthermore, water absorbed during absorption of the carbon dioxide must be removed.

Accordingly, there is a need for a new and improved process for recovering nitrogen-methane streams which are essentially free of carbon dioxide.

An object of the present invention is to provide a new and improved process for the treatment of natural gas.

A further object of the present invention is to provide a new and improved process for recovering from natural gas a nitrogen-methane stream essentially free of carbon dioxide.

Another object of the present invention is to provide a new and improved process for recovering, from natural gas, methane essentially free of nitrogen and heavier components.

Figure 2:
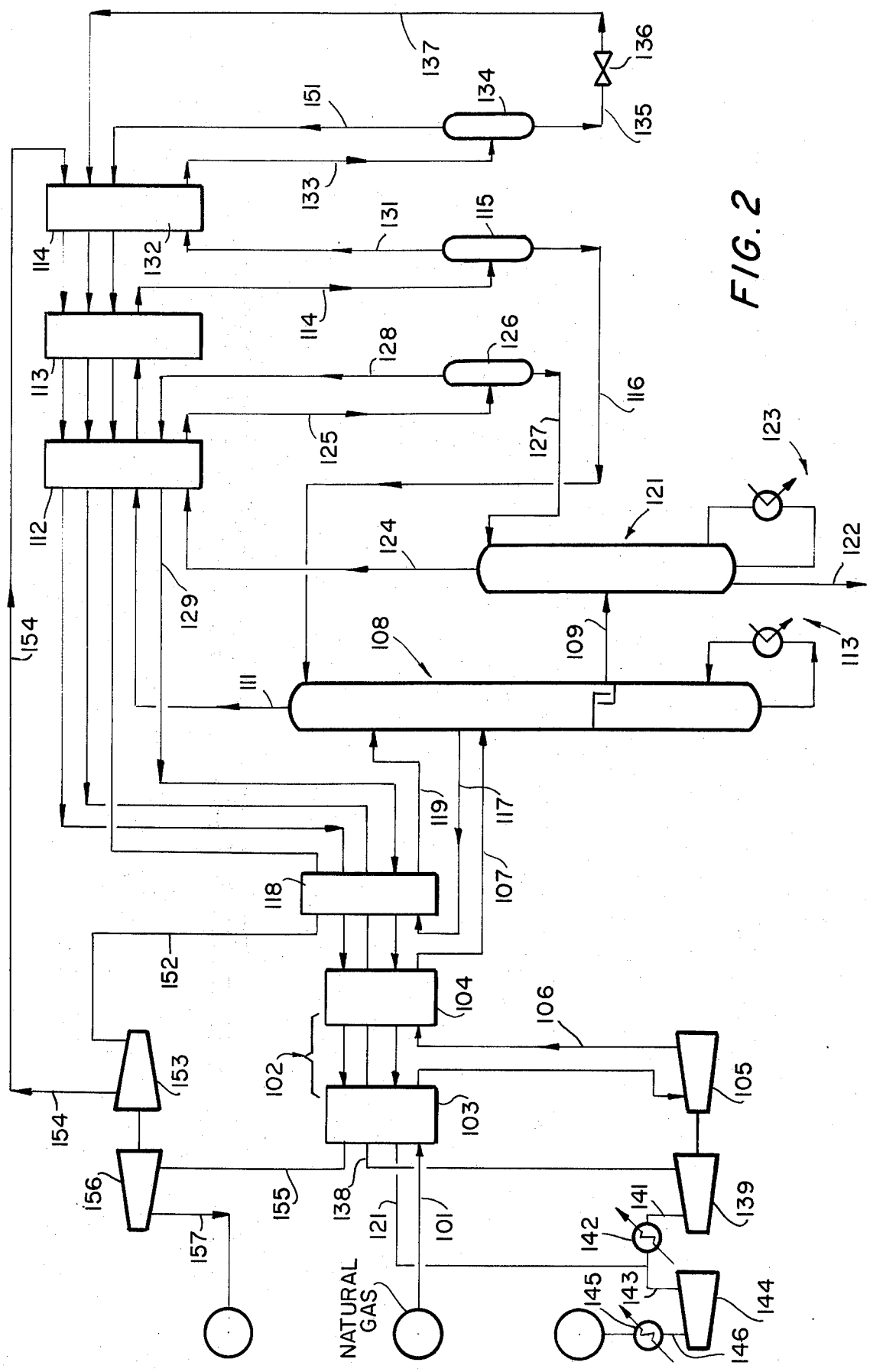

These and other objects of the present invention should become more readily apparent from reading the following detailed description thereof with reference to the accompanying drawings wherein:

FIG. 1 is a simplified schematic flow diagram of an embodiment of the present invention; and FIG. 2 is a simplified schematic flow diagram of a process for providing methane essentially free of nitrogen which incorporates the embodiment of FIG. 1.

In accordance with the present invention, there is provided a process for treating natural gas to recover a nitrogen-methane mixture, essentially free of carbon dioxide and materials heavier than methane, by employing two fractional distillation towers to effect such recovery. More particularly, the natural gas, containing methane, nitrogen, carbon dioxide and materials heavier than methane; i.e., $C_2$ + components, is introduced into a first fractional distillation zone operated at a temperature and pressure to produce an overhead of methane and nitrogen, essentially free of carbon dioxide and components heavier than methane. A sidestream is withdrawn from the first fractional distillation zone at a point therein where carbon dioxide concentration is maximized, and the side-stream is introduced, as feed, into a second fractional distillation zone, operated at a temperature and pressure to recover methane, as overhead. The first fractional distillation zone may be operated in a manner such that the bottoms therefrom is essentially free of carbon dioxide; i. e., essentially all of the carbon dioxide introduced with the natural gas is withdrawn in the sidestream. Similarly, the second fractional distillation zone may be operated in a manner such that essentially all of the carbon dioxide introduced therein is recovered with the methane overhead, whereby a bottoms is recovered therefrom which is essentially free of carbon dioxide. In this manner, the subsequent treatment system for recovering ethane from the bottoms from the first and second fractional distillation zones need not include a special means for removal of carbon dioxide. It is to be understood, however, that the first fractional distillation zone may be operated in a manner such that some carbon dioxide is recovered with the bottoms, provided that the overhead therefrom is essentially free of both carbon dioxide and components heavier than methane. Similarly, the second fractional distillation zone may be operated in a manner such that some of the carbon dioxide introduced therein is included in the bottoms.

In accordance with the present invention, the bottoms from the second fractional distillation zone will be considerably leaner in propane and heavier components than the bottoms from the first fractional distillation zone in that the liquid side-stream is withdrawn from the first fractional distillation zone at a point at which the $C_3+$ components are at a concentration less than that in the bottoms from the first fractional distillation zone. This partial separation of $C_2$ and $C_3$ hydrocarbons reduces the energy requirements for recovering ethane from the bottoms separated from the natural gas in the two distillation towers. Moreover, the use of the two fractional distillation tower system of the present invention, also eliminates the necessity of effecting nearly 100% ethane recovery in order to separate carbon dioxide by fractionation; i.e., the overhead from the second tower could contain some ethane, without adversely affecting recovery of a nitrogen-methane stream essentially free of carbon dioxide, which reduces utility requirements for the process.

In accordance with one embodiment of the present invention, the overhead from the fractional distillation zone comprised of nitrogen and methane, essentially free of carbon dioxide and components heavier than methane, is passed to a liquefaction system to recover therefrom a condensate consisting essentially of methane, and a nitrogen rich methane gas stream. This separation can be effected without the problems heretofore encountered in the art in that the nitrogen-methane stream employed as feed for the separation is essentially free of carbon dioxide. In accordance with a preferred embodiment, the cold potential of the liquefied methane stream, and the nitrogen enriched gaseous methane stream is recovered by using these streams for providing some of the cooling requirements for the process, such as, providing reflux cooling requirements for the first and second fractional distillation zones and also providing cooling requirements for the natural gas feed, prior to introduction thereof into the first fractional distillation zone.

This invention will be further described with respect to the accompanying drawings, but it is to be understood that the scope of the invention is not to be limited to the embodiments particularly described with reference to such drawings.

Referring now to FIG. 1, natural gas, containing methane, components heavier than methane, and minor portions of nitrogen and carbon dioxide, in line 10 is passed through a cooling zone, schematically indicated as 11, to effect cooling thereof to a temperature suitable for introduction into a fractional distillation zone for recovering a nitrogen-methane stream in accordance with the present invention. The cooling zone 11 may be comprised of one or more cooling and expansion stages, as known in the art, in order to effect the required cooling. The cooling zone 11 is provided with suitable refrigerant through line 11a. Natural gas, which may be partially liquefied, withdrawn from cooling zone 11, through line 12, is generally at a temperature from about −50°F to about −150°F, and at a pressure from about 600 to about 300 psig. The natural gas in line 12 is introduced into a first fractional distillation tower, schematically indicated as 13, operated at a temperature and pressure to recover, as overhead, a mixture of nitrogen and methane, which is essentially free of carbon dioxide and components heavier than methane. The fractional distillation column 13 is provided with line 14 for withdrawing a side-stream at a point therein at which the carbon dioxide concentration in column 13 is maximized. In accordance with a preferred aspect of this embodiment, the fractional distillation column 13 is operated in a manner such that the bottoms stream withdrawn through line 15 is also essentially free of carbon dioxide. In general, the fractional distillation column 13 is operated at an overhead temperature from about −130°F to about −200°F, a bottoms temperature from about 60°F to about 10°F and a pressure from about 600 to about 300 psi. It is to be understood, however, that the scope of the invention is not limited to such illustrative conditions.

An overhead of nitrogen and methane, essentially free of carbon dioxide and components heavier than methane, is withdrawn from tower 13 through line 16 and cooled in condenser 17, provided with a suitable refrigerant, to condense a portion thereof to meet reflux requirements for the top portion of tower 13. The stream withdrawn from condenser 17 is introduced into a liquid-gas separation vessel, schematically indicated as 18, and the condensed portion is returned as reflux, to the top tray of tower 13 through line 19. The uncondensed portion of the overhead, consisting essentially of nitrogen and methane, is withdrawn from vessel 18 through line 21. A bottoms stream comprised of $C_2$ and heavier hydrocarbons, preferably essentially free of carbon dioxide, is withdrawn from tower 13 through line 15. The heating requirements for the tower are provided by a suitable reboiler, schematically indicated as 22.

In accordance with a preferred feature of the present invention, the tower 13 is also provided with intermediate reflux. An intermediate vapor stream is withdrawn from tower 13 through line 23 at a point above the introduction of the feed 12 and at a point above withdrawal of the side-stream 14. The vapor in line 23 is passed through a condenser 24, provided with suitable refrigerant, and at least a portion thereof is condensed. A mixed vapor-liquid stream or liquid stream is withdrawn from condenser 24 through line 26 and introduced, as intermediate reflux, to the tower 13 at a point above the vapor stream withdrawal through line 23.

The side-stream (vapor and/or liquid) is withdrawn from tower 13, as hereinabove described, at a point where the carbon dioxide concentration is maximized. The side-stream in line 14, comprised of methane, carbon dioxide and components heavier than methane, which is essentially free of nitrogen, is introduced into a second fractional distillation tower, schematically indicated as 31. The tower 31 is operated at a temperature and pressure to produce a methane overhead which is essentially free of ethane and heavier components. It is to be understood, however, that in some cases the methane overhead may include some ethane and heavier hydrocarbon components in order to reduce the utility requirements for the fractionation. In accordance with a preferred aspect of the present invention, the tower 31 is operated in a manner such that the bottoms recovered therefrom is essentially free of carbon dioxide; i.e., essentially all of the carbon dioxide introduced in line 14 is withdrawn with the overhead. In accordance with the preferred aspect of the present invention, the tower 31 is generally operated at an overhead temperature from about −120°F to about −200°F, a bottoms temperature from about 60°F to about 0°F and a pressure from about 600 to about 300 psi. (It is to be understood, however, that the scope of the invention is not limited by such illustrative conditions.)

A bottoms stream, essentially free of methane, and preferably also essentially free of carbon dioxide, is withdrawn from tower 31 through line 32. The bottoms section of the tower is provided with a suitable reboiler, schematically indicated as 33, to provide heat requirements for the tower 31.

An overhead comprised of methane and carbon dioxide, essentially free of nitrogen, and generally also free of components heavier than methane, withdrawn from tower 31 through line 34, is passed through a condenser 35, provided with a suitable refrigerant, to condense a portion thereof to meet reflux requirements for the tower 31. The mixed vapor-liquid stream from condenser 35 is introduced into a gas liquid separator, schematically indicated as 36, and the condensed portion is returned to the top tray of tower 31, as reflux, through line 37. The uncondensed portion, consisting essentially of methane enriched with carbon dioxide, is withdrawn from vessel 36 through line 38.

The nitrogen and methane product recovered in line 21 may be employed as known in the art. For example, the stream in line 21 may be treated to reject nitrogen and recover a stream consisting essentially only of methane. Similarly the stream in line 38, may be used as a send-out gas as known in the art. The bottoms recovered in lines 15 and 32 may be further treated to recover ethane as known in the art. As hereinabove described, in accordance with the present invention, there has been a partial separation of $C_2$ components, in that the side-stream withdrawal through line 14 results in a bottoms in line 32 which is enriched in $C_2$ components. This partical separation reduces costs of a subsequent operation for recovering ethane as net product.

The present invention is particularly suitable for use in a process for separating ethane and heavier components from carbon dioxide containing natural gas in which nitrogen is to be rejected from the remaining methane in order to provide a send-out gas of proper heating value; i.e., a gas which includes a lower amount of inerts to compensate for the heating value lost by removal of ethane and heavier hydrocarbons from the gas. The use of the present invention in an overall process for separating ethane and heavier components from natural gas and providing a send-out gas essentially free of nitrogen is particularly described with respect to FIG. 2 of the drawings.

Referring now to FIG. 2, natural gas, containing methane, nitrogen, components heavier than methane and carbon dioxide, in line 101, at ambient temperature and a pressure which is generally at least 300 psig, is introduced into a first cooling stage, schematically indicated as 102, to cool the natural gas to a temperature suitable for demethanization. The first cooling stage 102, as particularly shown, is comprised of two sub-cooling stages 103 and 104 and a turbine 105 for expanding the gas. The cooling zone 102 is provided with returning gases, as hereinafter described, for indirectly cooling the natural gas stream. The natural gas in line 101 is passed through sub-cooling stage 103, wherein the gas is cooled to a temperature of from about 20°F to about −50°F, and is then passed through turbine 105, wherein the gas is expanded and cooled to a temperature of from about −10°F to about −80°F. The expanded gas, in line 106, is then passed through sub-cooling stage 104, wherein the natural gas is further cooled to a temperature of from about −50°F to about −150°F. The natural gas in line 107, from the cooling stage 102, is then introduced into a first fractional distillation tower, schematically indicated as 108. As hereinabove described, the tower 108 is operated in a manner such as to recover an overhead of nitrogen and methane, essentially free of carbon dioxide and components heavier than methane. The tower 108 is further provided with a line 109 for withdrawing a liquid and/or vapor side-stream at a point in the tower where the concentration of carbon dioxide is maximized. As hereinabove described, the tower 108 is preferably operated in a manner such that the bottoms recovered therefrom is also essentially free of carbon dioxide; i.e., essentially all of the carbon dioxide introduced through line 107 is withdrawn through side-stream line 109. An overhead stream essentially free of carbon dioxide and components heavier than methane, comprised of nitrogen and methane, is withdrawn from tower 108 through line 111.

A bottoms stream, essentially free of methane and nitrogen, and preferably also essentially free of carbon dioxide, is withdrawn from tower 108 through line 112. The bottoms stream 112 may be employed as known in the art; for example, passed to a deethanizer for recovery of ethane. The reboil requirements for the tower 108 are provided by a suitable reboiler, schematically indicated as 113.

The reflux requirements for the tower 108 are provided by passing the overhead in line 111 through a second cooling stage, schematically indicated as 112, and a third cooling stage, schematically indicated as 113, wherein the overhead is indirectly cooled, as hereinafter described, to condense a portion of the overhead and thereby meet the top reflux requirements for tower 108. A mixed vapor-liquid stream, from the third cooling stage 113, in line 114, generally at a temperature from about −130°F to about −200°F, and a pressure from about 600 to about 300 psig is introduced into a vapor-liquid separation vessel, schematically indicated as 115. The condensed portion is withdrawn from vessel 115 through line 116 and returned to the top tray of tower 108, as reflux.

The tower 108 is also preferably provided with an intermediate reflux. A vapor product is withdrawn from the tower 108 through line 117, at a point above the introduction of feed through line 107, and above the point of side-stream withdrawal through line 109, and is passed through a condenser 118, wherein the vapor is indirectly cooled, as hereinafter described, to condense a portion of the vapor side-stream. The mixed liquid and vapor or liquid withdrawn from condenser 118, through line 119, is reintroduced into tower 108, at a suitable tray to meet intermediate reflux requirements.

The side-stream, in line 109, comprised of methane, components heavier than methane and carbon dioxide, essentially free of nitrogen, is introduced into a second fractional distillation tower, schematically indicated as 121. As hereinabove described, the tower 121 is operated at a temperature and pressure to recover methane, essentially free of components heavier than methane, as overhead product. In accordance with one aspect of the present invention, the tower 121 is operated in a manner such that the bottoms recovered therefrom is essentially free of carbon dioxide. In accordance with this aspect of the invention, the tower 121 is generally operated at an overhead temperature from about −120°F to about −200°F, a bottoms temperature from about 60°F to about 0°F, and a pressure from about 600 to about 300 psig. It is to be understood, however, that the tower 121 may be operated in a manner such that carbon dioxide is present in the bottoms streams, and also in a manner such that some ethane is present in the overhead recovered therefrom.

A bottoms stream, essentially free of methane, and also preferably, essentially free of carbon dioxide is withdrawn from tower 121 through line 122. The bottoms in line 122 may be further treated as known in the art; for example, to recover ethane therefrom. It should be readily apparent that the use of the two fractional distillation towers also produces a partial separation of the $C_2$ and $C_3$ components of the natural gas in that the side stream withdrawn from tower 108 through line 109 contains less $C_3$ hydrocarbons than the bottoms stream withdrawn through line 112. The reboil requirements for tower 121 are provided by a suitable reboiler, schematically indicated as 123.

An overhead, comprised of methane and carbon dioxide, and preferably essentially free of components heavier than methane, is withdrawn from tower 121 through line 124, and passed through the second cooling stage, schematically indicated as 112, wherein the overhead is indirectly cooled, as hereinafter described, to condense a portion of the overhead to provide reflux for tower 121. The mixed vapor-liquid stream, from cooling stage 112, in line 125, is introduced into a vapor-liquid separation vessel, schematically indicated as 126. The condensed portion is withdrawn from vessel 126 through line 127, and introduced onto the top tray, as reflux for tower 121.

The uncondensed portion of the overhead from tower 121, comprised of methane and carbon dioxide, is withdrawn from vessel 126, through line 128, and then treated to recover the cold potential therefrom. More particularly, the vapor stream in line 128 is passed through the second cooling stage, schematically indicated as 112, to cool the overhead from towers 108 and 121. The vapor from the second cooling stage 112, in line 129, is then passed through the condenser 118 to indirectly cool the sidestream from tower 108, in line 117, and then through the substages 104 and 103 of the first cooling stage 102 to indirectly cool the natural gas feed to tower 108. In this manner, the caloric potential of the carbon dioxide enriched methane vapor in line 128 is recovered by providing a portion of the cooling requirements for the second cooling stage 112, the condenser 118, and the first cooling stage 102. The carbon dioxide enriched methane vapor, withdrawn from the subcooling stage 103 through line 121 is generally at ambient temperature.

The uncondensed portion of the overhead from tower 108, withdrawn from vessel 115, through line 131, may then be treated to recover a methane stream essentially free of nitrogen in order to improve the heating value of a send-out gas. More particularly, the gaseous stream in line 131 is passed through a fourth cooling stage, schematically indicated as 132, wherein the gaseous stream is indirectly cooled, as hereinafter described, to condense a major portion of the methane. The mixed vapor-liquid stream is withdrawn from the fourth cooling stage 132, through line 133, at a temperature of from about −200°F, to about −250°F, and a pressure of from about 250 to about 500 psig, and is introduced into a vapor-liquid separation vessel schematically indicated as 134, to separate the condensed methane portion.

The condensed methane portion, recovered in separation vessel 134, is withdrawn through line 135 and throttled in throttling valve 136. The throttled liquid stream in line 137, consisting essentially only of methane, is then treated to recover the cold potential therefrom. More particularly, the liquid stream in line 137 is passed, respectively, through the fourth cooling stage 132, to indirectly cool the methane-nitrogen stream in line 131, the third cooling stage 113, to cool overhead from tower 108, the second cooling stage 112 to cool overhead from towers 108 and 121, the condenser 118 to cool the sidestream from tower 108 in line 117, and the sub-cooling stages 104 and 103 of the first cooling stage 102 to cool the natural gas feed to tower 108. The nitrogen free methane stream, withdrawn from the sub-cooling stage 103 through line 138 (generally at about ambient temperature and a pressure of 100 to 350 psig), is introduced into a compressor, schematically indicated as 139, which is operated by expansion turbine 105. The compressed methane gas, from compressor 139, in line 141, is passed through a heat exchanger, schematically indicated as 142, to remove the heat of compression and combined with the carbon dioxide enriched methane stream in line 121. The combined stream, in line 143, is introduced into a compressor 144, to compress the combined stream to pipeline pressure. The compressed gas is passed through cooler 145 to remove the heat of compression and is then employed, in line 146, as a send-out gas of proper heating value.

The uncondensed portion of the overhead from tower 108 separated in vessel 134, is withdrawn through line 151 and treated to recover the caloric potential thereof. More particularly, the gas in line 151 is passed, respectively, through the fourth cooling stage 132 to indirectly cool the nitrogen-methane stream in line 131, the third cooling stage 113 to cool overhead from tower 108, the second cooling stage 112, to cool overhead from towers 108 and 121, and the condenser 118 to cool the side-stream from tower 108 in line 117. The heated gas, withdrawn from condenser 118, through line 152, at a temperature from about −55°F to about −155°F, and a pressure from about 600 to about 300 psig, which has provided a portion of the cooling requirements for the second, third and fourth cooling stages and the condenser 118, is then expanded in turbine 153 to a pressure of from about 100 to about 5 psig and a temperature of from about −200°F to about −260°F. The expanded gas, from turbine 153, in line 154, is then passed respectively, through the fourth cooling stage 132, the third cooling stage 113, the second cooling stage 112, the condenser 118, the sub-cooling stages 104 and 103 of the first cooling stage 102 to provide a portion of the cooling requirements for the respective stages and the condenser. The use of the expanded gas in line 154, in the fourth cooling stage 132, provides the positive temperature difference required to cool the gas in line 131 to a temperature suitable for effecting the nitrogen-methane separation in vessel 134. As a result, the liquid in line 135 can be throttled to a higher pressure.

The reheated nitrogen enriched gas, withdrawn from subcooling stage 103, through line 155, (generally at ambient temperature and a pressure of from 0 to 95 psig), is then compressed in compressor 156, operated by turbine 153. The compressed gas, in line 157, may then be used as a fuel. More particularly, the gas in line 157 is employed to meet the fuel requirements for the plant and, accordingly, the process is preferably designed to produce expanded nitrogen enriched gas in line 157 at the quantity required to meet such fuel requirements.

The present invention is particularly advantageous in that carbon dioxide is separated from a natural gas without the necessity of using an acid gas absorption system which lowers overall capital and operating expenses. In addition, such separation is effected without requiring 100% recovery of $C_2$ and heavier components from the natural gas. In addition, the subsequent processing of the heavier components recovered from the natural gas does not require removal of carbon dioxide in that the carbon dioxide is returned with the send-out gas. Moreover, the process takes advantage of the cold potential of the various streams to provide cooling requirements.

These advantages and other should be apparent to those skilled in the art from the teachings herein.

Numerous modifications and variations of the present invention are possible in light of the above teachings and, therefore, within the scope of the appended claims the invention may be practiced otherwise than as particularly described.

What is claimed is:

1. A process for recovering a nitrogen-methane mixture from natural gas containing methane, nitrogen, carbon dioxide and materials heavier than methane, comprising:

introducing the natural gas containing methane, nitrogen, carbon dioxide and materials heavier than methane into a first fractional distillation zone;

fractionally distilling the natural gas in the first fractional distillation zone to recover solely by fractional distillation a first overhead consisting essentially of nitrogen and methane, essentially free of carbon dioxide and materials heavier than methane, and a first bottoms of materials heavier than methane and essentially free of methane;

withdrawing a side-stream from the first fractional distillation zone at a point therein having a maximum concentration of carbon dioxide, said side-stream containing methane, carbon dioxide and materials heavier than methane, said side-stream being essentially free of nitrogen;

introducing the side-stream into a second fractional distillation zone; and fractionally distilling the side-stream in the second fractional distillation zone to recover an overhead containing carbon dioxide and methane and a bottoms containing materials heavier than methane.

2. The process of claim 1 wherein the first fractional distillation zone is operated at an overhead temperature from −130°F to −200°F, a bottoms temperature from 10°F to 60°F and a pressure from 300 to 600 psig, and the second fractional distillation zone is operated at an overhead temperature of from −120°F to −200°F, a bottoms temperature of from 10°F to 60°F and a pressure of from 300 to 600 psig, with essentially all of the carbon dioxide which is introduced into the second fractional distillation zone being recovered with the methane overhead.

3. The process of claim 2 wherein the first fractional distillation zone is provided with intermediate reflux at a point therein above both the point of introduction of the natural gas and the point of withdrawal of the side-stream.

4. The process of claim 3 wherein the natural gas is introduced into the first fractional distillation zone at a temperature of from −50° to −150°F and a pressure of from 300 to 600 psig.

5. A process for recovering methane from natural gas containing methane, carbon dioxide, nitrogen and materials heavier than methane, comprising;
   a. introducing the natural gas containing methane, carbon dioxide, nitrogen and materials heavier than methane into a first fractional distillation zone;
   b. fractionally distilling the natural gas in the first fractional distillation zone to recover solely by fractional distillation a first overhead consisting essentially of methane and nitrogen essentially free of carbon dioxide and materials heavier than methane, and a first bottoms containing materials heavier than methane and essentially free of methane and nitrogen;
   c. withdrawing a side-stream from the first fractional distillation zone at a point therein having a maximum concentration of carbon dioxide, said side-stream containing methane, carbon dioxide and materials heavier than methane and being essentially free of nitrogen;
   d. introducing the side-stream into a second fractional distillation zone;
   e. fractionally distilling the side-stream in the second fractional distillation zone to recover a second overhead containing methane and carbon dioxide and a second bottoms containing materials heavier than methane; and
   f. cooling first overhead from the first fractional distillation zone to condense a major portion of the methane and to produce a liquid methane stream essentially free of nitrogen.

6. The process of claim 5 wherein the first fractional distillation zone is operated at an overhead temperature from −130°F to −200°F, a bottoms temperature from 10°F to 60°F and a pressure from 300 to 600 psig, and the second fractional distillation zone is operated at an overhead temperature of from −120°F to −200°F, a bottoms temperature of from 10°F to 60°F and a pressure of from 300 to 600 psig, with essentially all of the carbon dioxide which is introduced into the second fractional distillation zone being recovered with the methane overhead.

7. The process of claim 6 wherein the first fractional distillation zone is provided with intermediate reflux at a point therein above both the point of introduction of the natural gas and the point of withdrawal of the side-stream.

8. The process of claim 6 wherein methane essentially free of nitrogen recovered from the first fractional distillation zone and methane overhead containing carbon dioxide from the second fractional distillation zone are combined to provide a send-out gas.

9. The process of claim 6 wherein the natural gas is introduced into the first fractional distillation zone at a temperature of from −50°F to −150°F and a pressure of from 300 to 600 psig.

10. The process of claim 6 wherein an uncondensed portion of the first overhead is recovered from step (f), expanded and employed to provide a portion of the cooling requirements for condensing a major portion of the methane from the first overhead.

11. The process of claim 10 wherein the first overhead is cooled to a temperature of from −200°F to −250°F at a pressure of from 250 to 600 psig to condense a major portion of the methane.

12. The process of claim 6 wherein the natural gas is cooled in a first cooling stage to a temperature of from −50°F to −150°F at a pressure of from 300 to 600 psig, prior to being introduced into the first fractional distillation zone; first overhead is passed through a second and third cooling stage to condense a portion thereof to provide reflux requirements for the first fractional distillation zone, the uncondensed portion of the first overhead from the third cooling stage being passed through a fourth cooling stage to effect said cooling to condense the major portion of the methane and produce said liquid methane stream essentially free of nitrogen, the liquid methane stream being throttled and passed through the fourth, third, second and first cooling stages to meet a portion of the cooling requirements; uncondensed first overhead being passed through the fourth, third and second cooling stages to provide a portion of the cooling requirements therefor, said uncondensed portion of the first overhead then being expanded and passed through the fourth, third, second and first cooling stages to provide a further portion of the cooling requirements therefor; second overhead being passed through the second cooling stage to condense a portion thereof to provide reflux requirements for the second fractional distillation zone; and uncondensed second overhead being passed through the second and first cooling stages to provide a portion of the cooling requirements therefor.

13. The process of claim 12 wherein methane essentailly free of nitrogen after passage through the first cooling stage, and uncondensed second overhead after passage through the first cooling stage are combined to provide a send-out gas.

14. The process of claim 13 and further comprising:
withdrawing a vapor side-stream from the first fractional distillation zone at both a point above the carbon dioxide side-stream withdrawal and a point above the introduction of natural gas into the first fractional distillation zone;
passing the vapor side-stream through a condensation zone to condense at least a portion thereof;
returning the side-stream from the condensation zone to an intermediate portion of the first fractional distillation zone at a point above its withdrawal to provide further reflux therefor;
passing said methane stream essentially free of nitrogen, the expanded uncondensed portion of the first overhead and uncondensed second overhead through the condensation zone subsequent to passage through the second cooling stage and prior to passage through the first cooling stage to provide cooling requirements for the condensation zone.

* * * * *